US011334464B2

(12) United States Patent
Pena et al.

(10) Patent No.: US 11,334,464 B2
(45) Date of Patent: May 17, 2022

(54) APPARATUS FOR DETERMINING MOBILE APPLICATION USER ENGAGEMENT

(71) Applicant: Click Therapeutics, Inc., New York, NY (US)

(72) Inventors: Caroline Pena, New York, NY (US); Katie Nicole Rodammer, Jersey City, NJ (US)

(73) Assignee: Click Therapeutics, Inc., New York, NY (US)

( * ) Notice: Subject to any disclaimer, the term of this patent is extended or adjusted under 35 U.S.C. 154(b) by 0 days.

(21) Appl. No.: 17/264,801

(22) PCT Filed: Oct. 2, 2020

(86) PCT No.: PCT/US2020/054121
§ 371 (c)(1),
(2) Date: Jan. 30, 2021

(87) PCT Pub. No.: WO2021/067848
PCT Pub. Date: Apr. 8, 2021

(65) Prior Publication Data
US 2021/0248054 A1    Aug. 12, 2021

Related U.S. Application Data

(60) Provisional application No. 62/909,572, filed on Oct. 2, 2019.

(51) Int. Cl.
*G06F 3/00* (2006.01)
*G06F 11/34* (2006.01)
(Continued)

(52) U.S. Cl.
CPC ...... *G06F 11/3438* (2013.01); *G06F 3/04842* (2013.01); *G06F 11/327* (2013.01);
(Continued)

(58) Field of Classification Search
CPC ............. G06F 11/3438; G06F 3/04842; G06F 11/327; G06F 3/04895; G06F 3/0482;
(Continued)

(56) References Cited

U.S. PATENT DOCUMENTS 5,207,580 A * 5/1993 Strecher ................. G09B 19/00
40/107
5,596,994 A * 1/1997 Bro ........................ H04M 3/465
600/545

(Continued)

FOREIGN PATENT DOCUMENTS

WO    2014143371 A1    9/2014
WO    2016004425 A1    1/2016

OTHER PUBLICATIONS

Koester, Heidi, "Text entry rate for people with physical disabilities [Infographic]", KPR Koester Performance Research, Jun. 27, 2018, updated Apr. 25, 2019. (Year: 2019).*

(Continued)

*Primary Examiner* — Jennifer E Nichols
(74) *Attorney, Agent, or Firm* — Bochner IP, PLLC; Andrew D. Bochner

(57) ABSTRACT

A computer system for assessing click speed values and deviation thresholds in a remote computing environment comprising processor, computer-readable memory, computer-readable storage device, and program instructions stored on storage device for execution by the processor. The system includes determining the baseline click speed values for a user and the deviation thresholds for the user over the predetermined period of time; determining a subsequent click speed value each time a user makes a selection when prompted; comparing the subsequent click speed value to the baseline click speed values and the deviation thresholds; determining whether the subsequent click speed value presents a predetermined deviation from the baseline click speed (Continued)

values and the deviation thresholds; incrementing a recorded deviations for the predetermined deviation; if the recorded deviations exceeds a predetermined allowable number of deviations, present, on one or more screens of a user device, a warning message to the user.

13 Claims, 11 Drawing Sheets

(51) Int. Cl.
<table>
<tr><td>G06F 3/04842</td><td>(2022.01)</td></tr>
<tr><td>G06F 11/32</td><td>(2006.01)</td></tr>
<tr><td>G06Q 30/00</td><td>(2012.01)</td></tr>
<tr><td>G16H 20/00</td><td>(2018.01)</td></tr>
<tr><td>G06F 3/0482</td><td>(2013.01)</td></tr>
<tr><td>G16H 10/20</td><td>(2018.01)</td></tr>
</table>

(52) U.S. Cl.
CPC ......... *G06Q 30/0185* (2013.01); *G16H 20/00* (2018.01); *G06F 3/0482* (2013.01); *G16H 10/20* (2018.01)

(58) Field of Classification Search
CPC ............. B60W 2540/229; H04L 67/22; G06Q 30/0185; G06Q 10/10; G16H 20/00; G16H 10/20
See application file for complete search history.

(56) References Cited

U.S. PATENT DOCUMENTS

| | | | | |
|---|---|---|---|---|
| 5,813,863 A * | 9/1998 | Sloane | ................... | G09B 5/065 434/323 |
| 5,967,789 A * | 10/1999 | Segel | ................... | G16H 20/70 131/270 |
| 6,039,688 A * | 3/2000 | Douglas | ................... | G16H 20/70 600/300 |
| 6,452,617 B1 * | 9/2002 | Bates | ................... | G06F 3/038 715/744 |
| 8,540,517 B2 * | 9/2013 | Williams | ................... | G09B 19/00 706/14 |
| 9,369,537 B1 * | 6/2016 | Mathew | ................... | H04M 1/67 |
| 10,055,756 B2 * | 8/2018 | Greenzeiger | ...... | G06Q 30/0251 |
| 10,313,461 B2 | 6/2019 | Ju | | |
| 10,956,933 B2 * | 3/2021 | Greenzeiger | ...... | G06Q 30/0251 |
| 11,043,135 B2 * | 6/2021 | Chapman | ................... | G09B 5/00 |
| 11,103,161 B2 * | 8/2021 | Williams | ................... | H04W 4/029 |
| 11,159,643 B2 * | 10/2021 | Jain | ................... | H04L 67/18 |
| 11,194,888 B1 * | 12/2021 | Murphy | ................... | G16H 50/70 |
| 2001/0031451 A1 * | 10/2001 | Sander | ................... | G09B 7/00 434/236 |
| 2003/0186202 A1 * | 10/2003 | Isenberg | ................... | G09B 19/00 434/236 |
| 2004/0247748 A1 * | 12/2004 | Bronkema | ......... | G09B 19/0076 426/8 |
| 2007/0072156 A1 * | 3/2007 | Kaufman | ................... | G16H 20/60 434/236 |
| 2007/0139362 A1 * | 6/2007 | Colton | ................... | G16H 40/67 345/156 |
| 2008/0162475 A1 * | 7/2008 | Meggs | ................... | G06Q 30/02 |
| 2009/0132275 A1 * | 5/2009 | Jung | ................... | G16H 40/67 600/300 |
| 2010/0003653 A1 * | 1/2010 | Brown | ................... | G09B 5/00 434/236 |
| 2011/0125739 A1 * | 5/2011 | Wexler | ................... | G06F 16/9577 707/723 |
| 2012/0258691 A1 * | 10/2012 | Baer | ................... | G06F 3/0481 455/412.2 |
| 2013/0018697 A1 * | 1/2013 | Giuffrida | ................... | G06Q 10/10 705/7.29 |
| 2014/0099614 A1 * | 4/2014 | Hu | ................... | G09B 19/00 434/236 |
| 2014/0121559 A1 * | 5/2014 | Stevens | ................... | A61B 5/7275 600/300 |
| 2014/0142967 A1 * | 5/2014 | Bedrosian | ................... | G16H 10/20 705/2 |
| 2014/0157171 A1 * | 6/2014 | Brust | ................... | G06F 16/285 715/771 |
| 2014/0244572 A1 * | 8/2014 | Hill | ................... | G06F 16/958 707/603 |
| 2014/0278308 A1 * | 9/2014 | Liu | ................... | H04N 21/23424 703/6 |
| 2015/0025997 A1 * | 1/2015 | Tilenius | ................... | G06F 16/90324 705/26.7 |
| 2015/0112796 A1 * | 4/2015 | Greenzeiger | ...... | G06Q 30/0251 705/14.49 |
| 2016/0026241 A1 * | 1/2016 | Leung | ................... | G06F 3/012 345/156 |
| 2016/0225272 A1 * | 8/2016 | Shea | ................... | G09B 7/06 |
| 2018/0349583 A1 * | 12/2018 | Turgeman | ......... | G06Q 20/40145 |
| 2018/0365619 A1 * | 12/2018 | Hardy | ................... | G06F 21/6254 |
| 2019/0057009 A1 * | 2/2019 | Wang | ................... | G06F 11/3438 |
| 2019/0114649 A1 * | 4/2019 | Wang | ................... | G06Q 30/0248 |
| 2019/0139082 A1 * | 5/2019 | Golan | ................... | G06Q 30/0243 |
| 2019/0155624 A1 * | 5/2019 | Lu | ................... | G06F 3/04883 |
| 2019/0189025 A1 * | 6/2019 | Angelopoulos | ......... | G16H 50/20 |
| 2019/0294522 A1 | 9/2019 | Prasher | | |
| 2019/0303537 A9 * | 10/2019 | Yim | ................... | G16H 40/67 |
| 2019/0339849 A1 * | 11/2019 | Williams | ............. | G06F 1/1626 |
| 2019/0359223 A1 * | 11/2019 | Duale | ................... | B60Q 9/00 |
| 2020/0126645 A1 * | 4/2020 | Robbins | ................... | G16H 50/30 |
| 2020/0152305 A1 * | 5/2020 | Pelliccioni | ............. | G16H 20/10 |
| 2020/0327821 A1 * | 10/2020 | Holzheimer | ............. | G09B 5/00 |
| 2021/0067544 A1 * | 3/2021 | Taylor | ................... | G06Q 30/02 |

OTHER PUBLICATIONS

Search report, dated Jan. 25, 2021, International Searching Authority, for application PCT/US2020/054121.

* cited by examiner

```
(venv) anton@dh-118:/var/www/pythonProject$ python main.py
===Enter data===
Enter age => 65
Enter Weight => 290
Enter Health condition => spinal cord injury
Calculating deviation allowances...
NO WARNINGS
===Result at morning===
Age => 65
Weight => 290
Health condition => spinal cord injury
===Deviation allowances===
{'Da1': 2, 'Da2': 2, 'Da3': 3}
===Time prompt===
2020-09-28 14:32:21.241512
===Time user clicks===
2020-09-28 14:32:49.246532
===Baseline speeds===
{'evening': {'CS_EF': None, 'CS_EM: None}, 'afternoon': {'CS_AF': None, 'CS_AM': None}, 'morning': {'CS_MF': 28, 'CS_MM': 28}}
===Lower Deviation threshold===
{'DT_U': 64.25, 'DT_L': -8.25}
```

*FIG. 3A*

```
//File: HealthTracker.py
from datetime import datetime
```
*# class HearthTracker*
```
class HealthTracker(object):
    age = 0
```
*# age:int*
```
    weight = 0
```
*# weight:int*
```
    health_condition = ''
```
*# health_condition:string*
```
    deviation_allowances = {
```
*# deviation_allowances:dictionary*
```
        "Da1": 0,
        "Da2": 0,
        "Da3": 0,
    }
    baseline_speeds = {
```
*# baseline_speeds:dictionary*
```
        "morning": {
            "CS_MM": None,
            "CS_MF": None,
        },
        "afternoon": {
            "CS_AM": None,
            "CS_AF": None,
        },
        "evening": {
            "CS_EM": None,
            "CS_EF": None
        }
    }
```

*FIG. 3B*

```
tc_1 = None  # time point after prompt is displayed
tc_2 = None  # time point after prompt is clicked
lower_deviation_threshold = {  # lower_deviation_threshold:dictionary
    "DT_U": 0,
    "DT_L": 0,
}
warning_counts = {  # warning_counts:dictionary
    "WA_X": 0,
    "WB_X": 0,
    "WC_X": 0
} def start(self, time=""):
    """
    Start function.
    :param time:string -> daytime
    :return:void
    """
    self.prompt_values()  # calling prompt_values function
    self.calculate_deviation_allowances()  # calling calculate_deviation_allowances function
    self.calculate_baseline_speeds(time)  # calling calculate_baseline_speeds function
    self.calculate_lower_deviation_threshold(time)  # calling calculate_lower_deviation_threshold function
    self.check_occurs(time)  # calling check_occurs function
    self.get_values(time)  # calling get_values function
```

*FIG. 3C*

```
def prompt_values(self):
    """
    Displaying prompt to user.
    :return:void
    """
    self.tc_1 = datetime.now() # get the prompt display time
    print "===Enter data==="
    self.age = raw_input("Enter age => ")
    self.weight = raw_input("Enter Weight => ")
    self.health_condition = raw_input("Enter Health condition => ")
    self.tc_2 = datetime.now() # get the end time of the user's response def get_values(self, time):
    """
    Print values.
    :param time:string -> daytime
    :return:void
    """
    print "===Result at " + time + "==="
    print "Age => " + self.age
    print "Weight => " + self.weight
    print "Health condition => " + self.health_condition
    print "===Deviation allowances==="
    print self.deviation_allowances
    print "===Time prompt==="
    print self.tc_1
```

FIG. 3D

```
print "===Time user clicks==="
print self.tc_2
print "===Baseline speeds==="
print self.baseline_speeds
print "===Lower Deviation threshold==="
print self.lower_deviation_threshold def calculate_deviation_allowances(self):
    """

Calculating Deviation Allowances (Da1, Da2, Da3).
    :return:void

"""
    print "Calculating deviation allowances..."

if self.age > 55: self.deviation_allowances["Da1"] = 1
    if self.age > 75: self.deviation_allowances["Da1"] = 2 if self.weight > 250: self.deviation_allowances["Da2"] = 1
    if self.weight > 350: self.deviation_allowances["Da2"] = 2 if self.health_condition == "arthritis": self.deviation_allowances["Da3"] = 1
    if self.health_condition == "cerebral palsy": self.deviation_allowances["Da3"] = 2
    if self.health_condition == "spinal cord injury": self.deviation_allowances["Da3"] = 3 def calculate_baseline_speeds(self, time):
    """
```

*FIG. 3E*

*Calculating baseline speeds (CSxx).*

*:param time:string -> daytime*

*:return:void*

"""

if time is "morning": key = "CS_M"

if time is "afternoon": key = "CS_A"

if time is "evening": key = "CS_E"

self.baseline_speeds[time][key + "M"] = (self.tc_2 - self.tc_1).seconds self.baseline_speeds[time][key + "F"] = (self.tc_2 - self.tc_1).seconds def calculate_lower_deviation_threshold(self, time):

"""

*Calculating lower and upper deviation threshold (DTu, DTl).*

*:param time:string -> daytime*

*:return:void*

"""

k = 5 if time is "morning": key = "CS_M"

if time is "afternoon": key = "CS_A"

if time is "evening": key = "CS_E"

*FIG. 3F*

```python
        self.lower_deviation_threshold['DT_U'] = self.baseline_speeds[time][key + "M"] + k
* (self.deviation_allowances['Da1'] + self.deviation_allowances['Da2'] +
self.deviation_allowances['Da3'] + 0.25)

self.lower_deviation_threshold['DT_L'] = self.baseline_speeds[time][key + "F"] - k *
(self.deviation_allowances['Da1'] + self.deviation_allowances['Da2'] +
self.deviation_allowances['Da3'] + 0.25)

def check_occurs(self, time):
        """
        Checking occurs (DTl < iCSxx < DTu).
        :param time:string -> daytime
        :return:void
        """
        if time is "morning": key = "CS_M"
        if time is "afternoon": key = "CS_A"
        if time is "evening": key = "CS_E"

if self.lower_deviation_threshold['DT_L'] < self.baseline_speeds[time][key + "M"]
and self.baseline_speeds[time][key + "M"] < self.lower_deviation_threshold['DT_U']:
            self.print_warning(time)

def print_warning(self, time):
        """
        Print a warning depending on the difference between iCSxx and DTx
        :param time:string -> daytime
        :return:void
        """
```

*FIG. 3G*

```
if time is "morning": key = "CS_M"
if time is "afternoon": key = "CS_A"
if time is "evening": key = "CS_E"
if self.baseline_speeds[time][key + "M"] < self.lower_deviation_threshold['DT_L']:
    if self.warning_counts['WA_X'] != 3:
        print "WARNING =====> A_1"
        self.warning_counts['WA_X'] += 1
    if self.warning_counts['WA_X'] == 3 and self.warning_counts['WB_X'] != 3:
        print "WARNING =====> B_1"
        self.warning_counts['WB_X'] += 1
    if self.warning_counts['WA_X'] == 3 and self.warning_counts['WB_X'] == 3:
        print "WARNING =====> C_1"
        self.warning_counts['WC_X'] += 1
elif self.baseline_speeds[time][key + "M"] > self.lower_deviation_threshold['DT_U']:
    if self.warning_counts['WA_X'] != 3:
        print "WARNING =====> A_2"
        self.warning_counts['WA_X'] += 1
    if self.warning_counts['WA_X'] == 3 and self.warning_counts['WB_X'] != 3:
        print "WARNING =====> B_2"
        self.warning_counts['WB_X'] += 1
    if self.warning_counts['WA_X'] == 3 and self.warning_counts['WB_X'] == 3:
        print "WARNING =====> C_2"
        self.warning_counts['WC_X'] += 1
else:
    print "NO WARNINGS"
```

*FIG. 3H*

//File: main.py from core import HealthTracker if name == " main ":
  ht = HealthTracker()
  ht.start(time="morning")
  ht.start(time="afternoon")
  ht.start(time="evening")

*FIG. 3I*

APPARATUS FOR DETERMINING MOBILE APPLICATION USER ENGAGEMENT

PRIORITY

The present application claims priority to U.S. Provisional Patent Application No. 62/909,572, which was filed in the United States Patent and Trademark Office on Oct. 2, 2019, the entire disclosure of which is incorporated herein by reference.

INTRODUCTION

Embodiments of the invention relate generally to apparatuses, systems, and methods for determining whether users of software are actively engaged and interacting with a software application. Such software may include applications that may be running on an electronic device including a smartphone, tablet, or the like.

Some users may be using certain software, for example, apps on a smartphone, tablet, or other device, without due care and/or adequate engagement. For example, users of apps or other software may not be carefully reading the prompts, carefully selecting their responses, paying attention to any images or storyline that may appear on their screens, responding to prompts or questions in a timely manner, responding to such prompts or questions too quickly, and the like.

However, it may be particularly important that users are engaged, especially when use of such software is recommended and/or prescribed by a medical professional and/or other clinician for the diagnosis or treatment of certain conditions such as insomnia or smoking cessation.

It would be desirable, therefore, to provide apparatuses, systems and methods for determining whether users of certain software are actively engaged and interacting with a software application as directed by their medical professional and/or clinician.

BRIEF DESCRIPTION OF THE DRAWINGS

FIG. 3A shows a screenshot of an electronic device that can implement one or more aspects of an embodiment of the invention; and FIGS. 3B-3I show source code that can implement one or more aspects of an embodiment of the present invention.

While the invention is described with reference to the above drawings, the drawings are intended to be illustrative, and the invention contemplates other embodiments within the spirit of the invention.

DETAILED DESCRIPTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Figure 1:
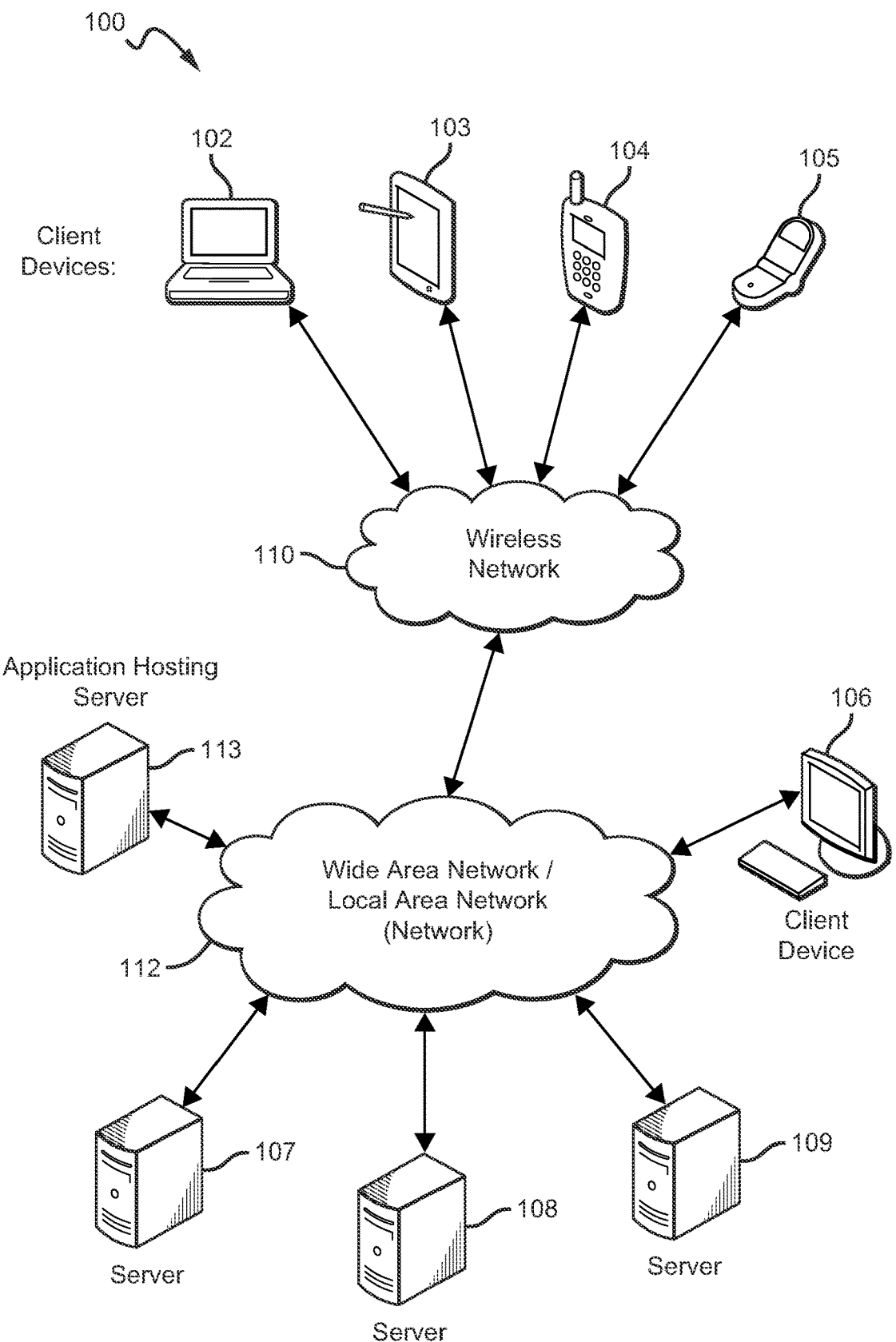
FIG. 1 illustrates a block diagram of a distributed computer system that can implement one or more aspects of an embodiment of the present invention.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-105, servers 107-109, and may include or communicate with one or more data stores or databases. Various of the client devices 102-106 may include, for example, desktop computers, laptop computers, set top boxes, tablets, cell phones, smart phones, smart speakers, wearable devices (such as the Apple Watch) and the like. The servers 107-109 can include, for example, one or more application servers, content servers, search servers, and the like. FIG. 1 also illustrates application hosting server 113.

Figure 2:
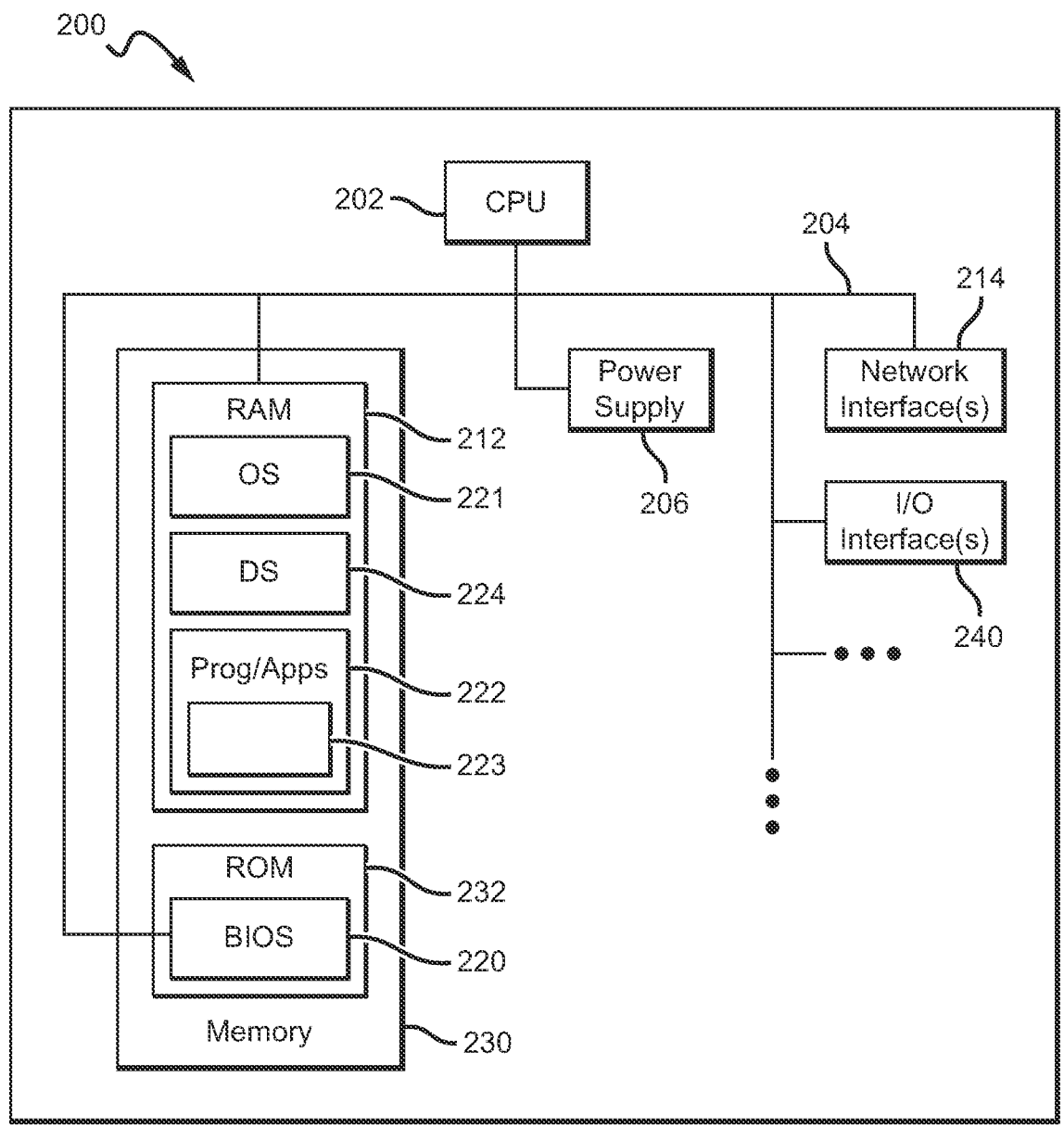
FIG. 2 illustrates a block diagram of an electronic device that can implement one or more aspects of an embodiment of the invention.

FIG. 2 illustrates a block diagram of an electronic device 200 that can implement one or more aspects of the apparatus for determining mobile application user engagement (the "Engine") according to one embodiment of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, cameras, heart rate sensors, light sensors, accelerometers, targeted biometric sensors, etc., which may be operable, for example, to provide graphical user interfaces or text user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the Engine program 223. The ROM 232 can also include Basic Input/Output System (BIOS) 220 of the electronic device.

Software aspects of the Engine program 223 are intended to broadly include or represent all programming, applications, algorithms, models, software and other tools necessary to implement or facilitate methods and systems according to embodiments of the invention. The elements may exist on a single computer or be distributed among multiple computers, servers, devices or entities.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the Engine, via a network to another device. Also, an application server may, for example, host a web site that can provide a user interface for administration of example aspects of the Engine.

Any computing device capable of sending, receiving, and processing data over a wired and/or a wireless network may act as a server, such as in facilitating aspects of implementations of the Engine. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server™, Mac OS X™, Unix™, Linux™, FreeBSD™, and the like.

A server may include, for example, a device that is configured, or includes a configuration, to provide data or content via one or more networks to another device, such as in facilitating aspects of an example apparatus, system and method of the Engine. One or more servers may, for example, be used in hosting a Web site, such as the web site www.microsoft.com. One or more servers may host a variety of sites, such as, for example, business sites, informational sites, social networking sites, educational sites, wilds, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for the apparatus, system and method embodying the Engine. Content may include, for example, text, images, audio, video, and the like.

In example aspects of the apparatus, system and method embodying the Engine, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers such as the Apple Watch and Fitbit, integrated devices combining one or more of the preceding devices, and the like.

Client devices such as client devices 102-106, as may be used in an example apparatus, system and method embodying the Engine, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, respiration sensors, body movement sensors, proximity sensors, motion sensors, ambient light sensors, moisture sensors, temperature sensors, compass, barometer, fingerprint sensor, face identification sensor using the camera, pulse sensors, heart rate variability (HRV) sensors, beats per minute (BPM) heart rate sensors, microphones (sound sensors), speakers, GPS or other location-aware capability, and a 2D or 3D touch-sensitive color screen on which both text and graphics may be displayed. In some embodiments multiple client devices may be used to collect a combination of data. For example, a smart phone may be used to collect movement data via an accelerometer and/or gyroscope and a smart watch (such as the Apple Watch) may be used to collect heart rate data. The multiple client devices (such as a smart phone and a smart watch) may be communicatively coupled.

Client devices, such as client devices 102-106, for example, as may be used in an example apparatus, system and method implementing the Engine, may run a variety of operating systems, including personal computer operating systems such as Windows™, iOS™ or Linux™, and mobile operating systems such as iOS™, Android™, Windows™ Mobile, and the like. Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the apparatus, system and method implementing the Engine, one or more networks, such as networks 110 or 112, for example, may couple servers and client devices with other computing devices, including through wireless network to client devices. A network may be enabled to employ any form of computer readable media for communicating information from one electronic device to another. The computer readable media may be non-transitory. A network may include the Internet in addition to Local Area Networks (LANs), Wide Area Networks (WANs), direct connections, such as through a Universal Serial Bus (USB) port, other forms of computer-readable media (computer-readable memories), or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in an example apparatus, system and method implementing the Engine, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in an example apparatus, system and method implementing the Engine, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

Embodiments of the present invention include apparatuses, systems, and methods implementing the Engine. Embodiments of the present invention may be implemented on one or more of client devices 102-106, which are communicatively coupled to servers including servers 107-109. Moreover, client devices 102-106 may be communicatively (wirelessly or wired) coupled to one another. In particular, software aspects of the above may be implemented in the Engine program 223. The Engine program 223 may be implemented on one or more client devices 102-106, one or more servers 107-109, and 113, or a combination of one or more client devices 102-106, and one or more servers 107-109 and 113.

Disclosed herein are apparatuses, systems and methods for determining whether users of software are actively engaged and interacting with a software application.

Pharmaceuticals are most likely to provide beneficial results when taken as prescribed, and patient compliance/adherence to medical treatment as prescribed by a clinician is an established problem in both clinical trials and the real world.

Another form of treatment in which patient compliance/adherence is important is one that consists of or includes interaction with an electronic device such as a smartphone, tablet, laptop, or the like (i.e., Digital Therapeutics (DTx)). Such treatment may be complementary to or may replace a pharmaceutical treatment. For example, if a patient is addicted to smoking, a clinician may prescribe a treatment of interacting with software running on an electronic device that monitors smoking by the patient.

For example, the software may determine the location of the user by using location services (such as a GPS receiver and associated software) of the electronic device. If the software determines that the user is in a location where the user, and/or the population as a whole, and/or the user's demographic, is more likely to smoke, the software may take certain actions such as activating a camera, activating a microphone, activating sensors that can determine the presence of smoke, reminding the user not to smoke by generating a message on the screen of the electronic device, asking the user if he or she is smoking by generating a message on the screen of the digital device, and the like.

However, a person that has been prescribed such treatment may simply click through any prompts and would thus not provide positive results. Moreover, simply clicking through or not being actively engaged would not provide accurate results as to the treatment's efficacy. For example, a user can easily click through an activity answering "yes" or "done" to activities that were never actually completed by the user.

Embodiments of the present invention measure adherence of a given treatment by, for example, measuring the user's click speed as they navigate through the modules of the application. To bridge the gap between adherence and engagement, embodiments of the present invention include algorithms to personalize compliance remediation techniques based on user demographics, click speed, and baseline user habits.

To summarize, according to certain embodiments of the present invention, when a user begins clicking faster or slower than certain pre-defined thresholds, alerts and messages will appear in the app in order to: (1) attract the user's attention; (2) alert the user that the software is monitoring their behavior since users are generally more compliant when they believe they are being monitored; and (3) encourage the user to modify their behavior to engage more actively with the software. This results in a more compliant user and more successful treatment.

More specifically, once a user is prescribed the treatment (i.e., interaction with software/app running on an electronic device such as a smartphone), the user will first input basic demographic information (e.g., age, weight, location, health history, and the like). During the first two (2) (or 1 or 3 or 4) weeks of treatment, baseline user habits are recorded by the software. These inputs will then be used to monitor threshold limits throughout the treatment. If a threshold is passed (e.g., user click speed is above or below a defined personal limit of that user), the software will deploy in-app alerts and messages to encourage the user to be more engaged with the product.

The in-app alerts and messages will be accessed from a library/database of messages, alerts, and educational information, stored either on the electronic device or on another device such a server communicatively coupled with the electronic device. User response to the app (i.e., determining whether alerts were effective and whether the user is more or less engaged) is assessed by the software, and similar types of alerts will be used on an ongoing basis to promote user treatment engagement if the app determines that the thresholds have been passed. On the other hand, if the software determines that alerts were ineffective, different alerts will be selected from the library/database to determine whether other alerts may be more effective at changing user behavior.

The following provides further detail regarding the software for determining whether users of software are actively engaged and interacting with a software application.

To quantify a user's engagement, an embodiment of the present invention first creates a user profile based on information collected from demographic questions and calculates baseline Click Speed (CS) values and Deviation Thresholds (DTs) for the user during the initial weeks (e.g., 2) of treatment. The software then detects when the CS, calculated as the user is interacting with the app, deviates above or below the DT. When deviations occur, users receive feedback in order to promote adherence and continued engagement with their treatment.

When a user first begins treatment, the user is asked questions about his or her age and physical disabilities. These factors are considered relevant when creating a baseline for a user as they could impact the speed at which a user interacts with a mobile app. For example, if a user is over 55 years old or has a physical disability that could affect their dexterity, such as brain or spinal cord injuries, cerebral palsy, arthritis and more, they may interact with a mobile app slower than an average person. The user's CS within the software is also recorded during this time and for the two weeks of treatment. CS is defined as the change in time according to the following equation (1): $CS = t_{C2} - t_{C1}$ According to the above equation (1), $t_{C2}$ is the time at which a user clicks on a feature (e.g., button, toggle, image, etc.) on a screen within the app and $t_{C1}$ is the time at which the user either first opened that screen (if $t_{C2}$ is the first time the user interacted with the screen since it was opened) or clicked on another feature (button, toggle, image, etc.) within that screen, if the user has already interacted with the screen.

Embodiments of the present invention include 2 types of program aspects that are relevant for treatment: (1) Missions, which are activities that mainly contain text for the user to read and some sections that require user interaction; and (2) Features, which are activities that mainly contain sections that require user interaction and some text. Because of their differences, CS is tracked for these two aspects separately as the speed at which a user interacts with them may differ.

In addition, time of day is also tracked, as users may exhibit differences in CS depending on time of day. For example, users may be more tired at 3 a.m. as opposed to 3 p.m. Thus, it is necessary to track the time of day and compare the user's CS to the baseline CS for that time of day.

These 2 considerations (differences in program features and time) lead to the creation of 6 CS baseline values per user: (1) $CS_{MM}$ (CS of interactions with Missions in the morning, or between the hours of 5 AM to 11:59:59 a.m. inclusive); (2) $CS_{MF}$ (CS of interactions with Features in the morning); (3) $CS_{AM}$ (CS of interactions with Missions in the afternoon, or between the hours of 12 p.m. to 5:59:59 p.m. inclusive); (4) $CS_{AF}$ (CS of interactions with Features in the afternoon); (5) $CS_{EM}$ (CS of interactions with Missions in the evening/night, or between the hours of 6 p.m. to 4:59:59 a.m. inclusive); and (6) $CS_{EF}$ (CS of interactions with DTx features in the evening/night). Deviation thresholds (DTs) were set to 5 seconds (faster or slower) per CS baseline as a default (i.e., Equation (2), DT for CS=CS±5 seconds). However, if users indicated factors that would impact their CS in their user profile, DTs were adjusted using the following equation (3):

$$DT \text{ for } CS = C \pm (5*(n+0.25)) \text{ seconds}$$

According to the above equation (3), CS is the click speed baseline value and n is the number of factors that could impact click speed that the user indicated in their profile in response to the initial question posed by the software.

For example, consider a user who is 30 years old with no physical disabilities, and has the following CS baseline values: $CS_{MM}$=62 seconds (s), 2; $CS_{MF}$=25 s, 3; $CS_{AM}$=50 s, 4; $CS_{AF}$=18 s, 5; $CS_{EM}$=55 s, 6; and $CS_{EF}$=20 s The DTs for the above would user would thus be as follows: DT for $CS_{MM}$=62±5 s, 2; DT for $CS_{MF}$=25±5 s, 3; DT for $CS_{AM}$=50±5 s, 4; DT for $CS_{AF}$=18±5 s, 5; DT for $CS_{EM}$=55±5 s, 6; DT for $CS_{EF}$=20±5 s.

That is, for example, with respect to $CS_{MM}$, applying equation (2), the result is 62±5 seconds.

However, if we had a user who had the same CS baseline values but was 60 years old and had arthritis (n=2) (i.e., +1 for being 55 years or older and +1 for having arthritis) their DTs would be: DT for $CS_{MM}$=62±11.25 s, 2. DT for $CS_{MF}$=25±11.25 s, 3. DT for $CS_{AM}$=50±11.25 s, 4. DT for $CS_{AF}$=18±11.25 s, 5. DT for $CS_{EM}$=55±11.25 s, 6. DT for $CS_{EF}$=20±11.25 s.

That is, for example, with respect to $CS_{MM}$, applying equation (3), 62±(5*(2+0.25)) s=62±11.25 s.

After the CS baseline values and DTs are calculated, comparisons between CS values are calculated each time the user interacts with the mobile app and DTs for the relevant time-of-day are made. Deviations from DTs are recorded for the user. For example, for the $CS_{MM}$ example for the 60 year old user with arthritis, discussed above, assuming the $CS_{MM}$ was more than 73.25 seconds or less than 50.75 seconds, a deviation would be determined and stored in a database, either on the electronic device or a database residing on a server communicatively coupled to the electronic device.

After a predetermined number (e.g., 3) of deviations are recorded for a user, a determination is made that the user is not properly engaging with the software. The user then receives a message randomly selected from a library containing alerts that warns the user of their behavior, and provides information on the importance of adhering to their treatment and humorous messages.

Some of the content in these messages is customized to the deviation behavior shown by the user (faster/slower clicks). For example, if the CS of the user discussed above is higher than 73.25 seconds, a message tailored for slow click speed is selected from the database. However, if the CS of the user discussed above is lower than 50.75 seconds, a message tailored for fast click speed is selected from the database.

The type of message displayed to the user on the screen of the electronic device is then recorded (e.g., alert, information, or humor).

After the first such message is displayed to the user, the software determines whether there is an ongoing problem of user engagement. If a predetermined number, e.g., 3, of additional deviations occur within the span of the next predetermined number, e.g., 7, of days, the user receives a message randomly selected from the other two types of messages. That is, for example, if the user was originally shown a message selected from the "humor" messages, either an "information" or an "alert" message would then be shown. This is so to attempt to determine a feedback method that would effectively promote user engagement on an individual basis. That is, if a "humor" message was not effective in promoting user engagement, it is then determined whether an "information" or "alert" message is effective.

For example, if the algorithm detects three deviations from a user and sends an information message to the user such as "Medication has best results when taken as prescribed. Likewise, engaging with this digital therapeutic is essential in ensuring you are receiving adequate treatment!" and 4 days later, the software detects another 3 deviations from the user, the user may then receive an alert message such as "You've been completing your missions faster than usual! Make sure you're reading through the missions completely!"

If, after the "alert" message, the user's CS does not deviate from the DTs for the next 7 days, the software would record alert messages as being an effective form of feedback method for promoting engagement. The software would also record that the "information" message is not an effective form of feedback method for promoting engagement. Thus, if the user then again begins to deviate from DTs, they would receive another "alert" message since it has been determined that alert messages are more effective than information messages.

The above embodiments generally relate to using CS to determine whether the user is adequately engaged. However, other factors may be used instead of or in conjunction with user CS.

For example, software running on an electronic device may determine the proportion of the time a user is looking at the relevant portion of the electronic device screen (i.e., eye tracking). For example, some smartphones allow picture-in-picture functionality, where the user may be interacting with one app (e.g., watching a movie or a TV show in the Netflix app) while also interacting with another app (e.g., an app prescribed by a clinician). In this case, although the CS may indicate that the user is actively engaged with the app prescribed by the clinician, the user may in fact have spent a portion of that time engaged with another app. That is, for example, if the app prescribed by the clinician is in a particular portion of the screen (e.g., the upper right quadrant), the app can determine that 80% of the relevant CS time was actually spent looking at the upper left, lower left, and/or lower right quadrants, engaging with another app such as Netflix.

In order to make the above determination, the app accesses a camera on the electronic device or another camera near the user, which takes one or more photographs or videos of the user, determines the location of the sclera, iris, pupil and other parts of one or both of the eyes of the user. The software takes regular photographs (for example, every 1 second or 0.5 seconds) and determines the point on the screen of the electronic device at which one or both eyes are focused. Once the point on the screen is determined, the software uses certain Application Programming Interfaces (APIs) provided by the electronic device to determine the app the user is focused on. The software then calculates the proportion of points the user was focused on that are on the clinician prescribed app. If the proportion of points is below a certain threshold (e.g., 75%), a determination is made that the user is not engaging with the clinician prescribed app.

In another embodiment, the software running on the electronic device may take multiple photos to determine whether the user is in motion. For example, the software may determine that the user is running or engaged in another activity during which the user would be unlikely to be actively engaged with the clinician prescribed app.

In yet another embodiment, the software running on the electronic device may activate a microphone to determine sounds that may make it unlikely that the user is actively engaged with the clinician prescribed software. For example, when determining user baselines, the app may record the user's voice. The app may then determine, by activating the microphone on the electronic device, whether the user is speaking, other people are speaking, music is playing, the user is attending an event, and the like. If the app determines that the user was speaking more than a certain proportion of the time, the app would determine a deviation.

FIGS. 3B-3I show source code that can implement one or more aspects of an embodiment of the present invention. FIGS. 3B-3I include: (1) a first algorithm that receives basic user inputs from the user. The algorithm asks for Age (A), Weight (W), and Health Condition (H) when run; (2) a second algorithm that sets "deviation allowances" (DA1, DA2, DA3). These numbers are set to zero by default but are calculated by the using formulas depending on A, W, and H parameters that were received by the algorithm (1); (3) a third algorithm that determines baseline speeds (CSxx) at which the user clicks a prompt (tc2) after the prompt is displayed (tc1), for a first type of prompt (CSxM) and a second type of prompt (CSxF), during the morning (CSMx), during the afternoon (CSAx) and during the evening (CSEx). The baselines may be calculated by average (CSxx) over the course of an initial time frame (TFI); (4) a fourth algorithm that sets an upper and lower deviation threshold (DTu, DTl) according to the formula; (5) a fifth algorithm that, after the baselines and deviation threshold are calculated, determines if a deviation occurs for a later instantiation by determining if the click speed of the instantiation (iCSxx) is not within the scope of the baseline by taking into account the deviation threshold; (6) a sixth algorithm that, if a deviation has occurred, transmits a warning to the user based on the type of deviation and the number of previous warnings given. FIG. 3A shows input and output relating to the source code.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. A computer system for assessing click speed values and deviation thresholds of a user interacting with a prescribed software application in a remote computing environment comprising
   one or more processors,
   one or more computer-readable memories, and
   one or more computer-readable storage devices,
   a library of warning messages stored on at least one of the one or more computer-readable storage devices, and
   program instructions stored on at least one of the one or more computer-readable storage devices for execution by at least one of the one or more processors via at least one of the one or more computer-readable memories,
   the stored program instructions comprising:
   providing an information input, via one or more screens of a user device, in the prescribed software application;
   collecting, from a user, a plurality of factors that impact click speed, via the information input on the one or more screens;
   calculating a plurality of deviation allowances for the plurality of factors, wherein each of the plurality of deviation allowances are zero by default;
   determining a plurality of baseline click speed values for the user over a predetermined period of time and determining a plurality of deviation thresholds for the user over the predetermined period of time,
   wherein the plurality of deviation thresholds is based on the plurality of baseline click speed values and the plurality of deviation allowances;
   following the determining of the plurality of baseline click speed values and determining the plurality of deviation thresholds for the user, determining a subsequent click speed value each time a user makes a selection when prompted with a prompt in the prescribed software application;
   comparing the subsequent click speed value to the plurality of baseline click speed values and the plurality of deviation thresholds;
   determining whether the subsequent click speed value presents a predetermined deviation from the plurality of baseline click speed values and the plurality of deviation thresholds;
   incrementing a recorded deviations for the predetermined deviation;
   if the recorded deviations exceed a predetermined allowable number of deviations, present, on the one or more screens of a user device, a first warning message to the user,
   wherein the first warning message is a type of warning message, and
   wherein the type of warning message comprises humor, information, or alert;

determining whether the type of warning message is effective in promoting user engagement based on the subsequent click speed value of the user deviating or not deviating from the plurality of baseline click speed values and the plurality of deviation thresholds;

if the type of warning message is not effective in promoting user engagement based on the subsequent click speed value of the user deviating from the plurality of baseline click speed values and the plurality of deviation thresholds, presenting a second type of warning message different from the type of warning message of the first warning message to the user;

determining, after a predetermined number of deviations are recorded, whether the subsequent click speed value is greater than the plurality of deviation thresholds; and if the subsequent click speed value is greater than the plurality of deviation thresholds, presenting to the user a randomly selected warning message from the library informing the user of their behavior and providing information on the importance of adhering to the prescribed software application.

2. The computer system according to claim 1, wherein the plurality of factors comprises age, location, weight, and physical disabilities of the user.

3. The computer system according to claim 2, wherein the physical disabilities include a physical disability affecting dexterity.

4. The computer click speed assessment system according to claim 2, wherein the physical disabilities include at least one of a brain injury, a spinal cord injury, cerebral palsy, or arthritis.

5. The computer system according to claim 1, wherein the determining a plurality of baseline click speed values for the user comprises determining a time at which the user responds to the prompt in the prescribed software application by clicking on a feature; determining a time at which the feature was displayed on the one or more screens to the user; determining a difference between the time at which the feature was displayed on the one or more screens to the user and the time at which the user clicks on the feature.

6. The computer system according to claim 1, wherein each of the plurality of baseline click speed values and the plurality of deviation thresholds for the user is determined for a plurality of different times of day.

7. The computer system according to claim 6, wherein the plurality of different times of day comprises morning, afternoon, evening, and night.

8. The computer system according to claim 1, wherein the plurality of deviation thresholds are determined based on a following formula: DT for $CS=CS\pm(5*(n+0.25))$ seconds, wherein DT is one of the plurality of deviation thresholds, CS is one of the plurality of baseline click speed values, and n is a number of factors of the plurality of factors that impact click speed collected from the user.

9. A computer implemented method for assessing click speed values and deviation thresholds of a user interacting with a prescribed software application in a remote computing environment, the method comprising:

providing an information input, via one or more screens of a user device, in the prescribed software application;

collecting, from a user, a plurality of factors that impact click speed, via the information input on the one or more screens;

calculating a plurality of deviation allowances for the plurality of factors, wherein each of the plurality of deviation allowances are zero by default;

determining a plurality of baseline click speed values for the user over a predetermined period of time and determining a plurality of deviation thresholds for the user over the predetermined period of time, wherein the plurality of deviation thresholds is based on the plurality of baseline click speed values and the plurality of deviation allowances;

following the determining of the plurality of baseline click speed values and determining the plurality of deviation thresholds for the user, determining a subsequent click speed value each time a user makes a selection when prompted with a prompt in the prescribed software application;

comparing the subsequent click speed value to the plurality of baseline click speed values and the plurality of deviation thresholds;

determining whether the subsequent click speed value presents a predetermined deviation from the plurality of baseline click speed values and the plurality of deviation thresholds;

incrementing a recorded deviations for the predetermined deviation;

if the recorded deviations exceed a predetermined allowable number of deviations, present, on one or more screens of a user device, a first warning message to the user, wherein the first warning message is a type of warning message, and wherein the type of warning message comprises humor, information, or alert;

determining whether the type of warning message is effective in promoting user engagement based on the subsequent click speed value of the user deviating or not deviating from the plurality of baseline click speed values and the plurality of deviation thresholds;

if the type of warning message is not effective in promoting user engagement based on the subsequent click speed value of the user deviating from the plurality of baseline click speed values and the plurality of deviation thresholds, presenting a second type of warning message different from the type of warning message of the first warning message to the user;

determining, after a predetermined number of deviations are recorded, whether the subsequent click speed value is greater than the plurality of deviation thresholds; and if the subsequent click speed value is greater than the plurality of deviation thresholds, the user then receives a randomly selected warning message from the library informing the user of their behavior and providing information on the importance of adhering to the prescribed software application.

10. The computer implemented method according to claim 9, wherein
the plurality of factors comprises age, location, weight, and physical disabilities of the user.

11. The computer implemented method according to claim 10, wherein the physical disabilities include a physical disability affecting dexterity.

12. The computer implemented method according to claim 10, wherein the physical disabilities include at least one of a brain injury, a spinal cord injury, cerebral palsy, or arthritis.

13. The computer implemented method according to claim 9, wherein the determining a plurality of baseline click speed values for the user comprises determining a time at which the user responds to the prompt in the prescribed software application by clicking on a feature;

determining a time at which the feature was displayed on the one or more screens to the user;

determining a difference between the time at which the feature was displayed on the one or more screens to the user and the time at which the user clicks on the feature.

* * * * *